United States Patent [19]

Andrew

[11] Patent Number: 5,160,323
[45] Date of Patent: Nov. 3, 1992

[54] METHOD AND SYSTEM FOR INSERTING SPINAL CATHETERS

[76] Inventor: Daniel E. Andrew, 524 Beechwood Drive, Unit 1, Waterloo Ontario, Canada, N2T 2G9

[21] Appl. No.: 656,153
[22] PCT Filed: May 24, 1990
[86] PCT No.: PCT/CA90/00169
   § 371 Date: Mar. 25, 1991
   § 102(e) Date: Mar. 25, 1991
[87] PCT Pub. No.: WO90/14124
   PCT Pub. Date: Nov. 29, 1990
[51] Int. Cl.5 .......................................... A61M 25/01
[52] U.S. Cl. ..................................... 604/158; 604/165
[58] Field of Search ................ 604/164, 165, 158, 163

[56] References Cited

U.S. PATENT DOCUMENTS

| | | | |
|---|---|---|---|
| 4,013,080 | 3/1977 | Froning | 604/165 |
| 4,191,186 | 3/1980 | Keeler | 604/164 |
| 4,192,305 | 3/1980 | Seberg | 604/165 |
| 4,362,156 | 12/1982 | Feller, Jr. et al. | 604/165 |
| 4,576,589 | 3/1986 | Kraus et al. | 604/165 |
| 4,642,101 | 2/1987 | Krolikowski et al. | 604/164 |
| 4,735,614 | 4/1988 | Yapp et al. | 604/165 |
| 4,946,443 | 8/1990 | Hauser et al. | 604/165 |
| 4,973,312 | 11/1990 | Andrew | 604/158 |
| 5,064,414 | 11/1991 | Revane | 604/165 |

Primary Examiner—Paul J. Hirsch
Attorney, Agent, or Firm—Stevens, Davis, Miller & Mosher

[57] ABSTRACT

A method and a system for inserting spinal catheters for administration of spinal anaesthesia are disclosed. An epidural needle (10) having a hub (22) is inserted into the epidural space of a patient and a cannula (18) having a blunt end (52) is inserted into and advanced forwardly within the epidural needle for abutment against the dura-arachnoid membrane (53) to place the membrane in tension. The cannula is locked in place in the epidural needle by a securing means (32) attached to the hub of the epidural needle. A flexible catheter (54) having a wire (58) or stylet therein with an end projecting beyond the distal end of the catheter is inserted through the cannula for piercing a hole in the tensioned dura-arachnoid membrane whereby the catheter can be inserted a predetermined distance through the dura-arachnoid membrane into the subarachnoid space. The cannula and epidural needle are removed and the wire withdrawn to allow continuous administering of an anaesthetic through the catheter. A hole can be formed in the dura-arachnoid membrane by a sharp stylet prior to insertion of the catheter.

18 Claims, 11 Drawing Sheets

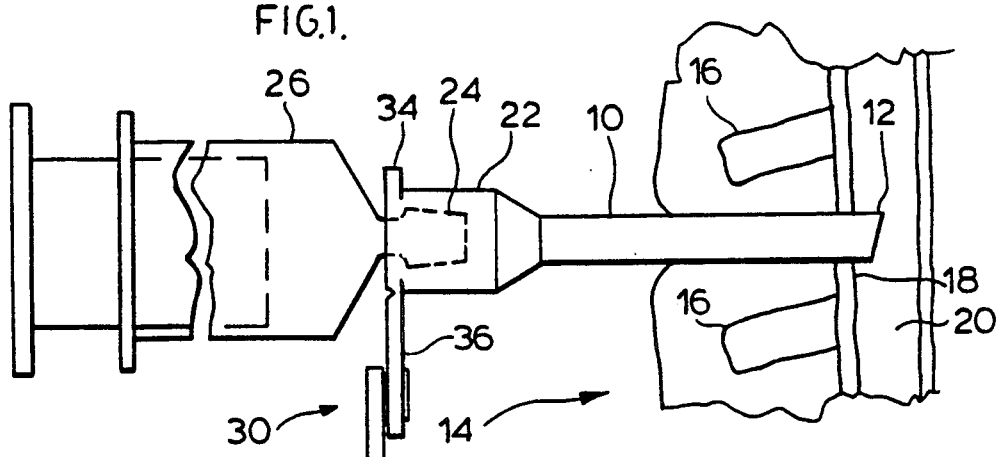
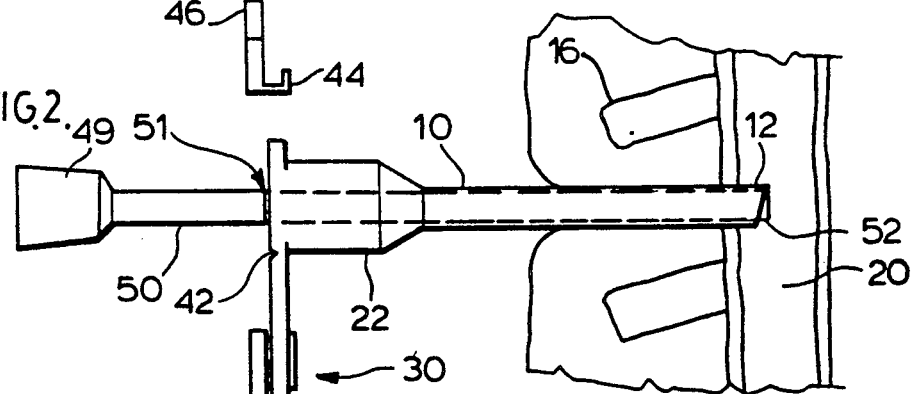
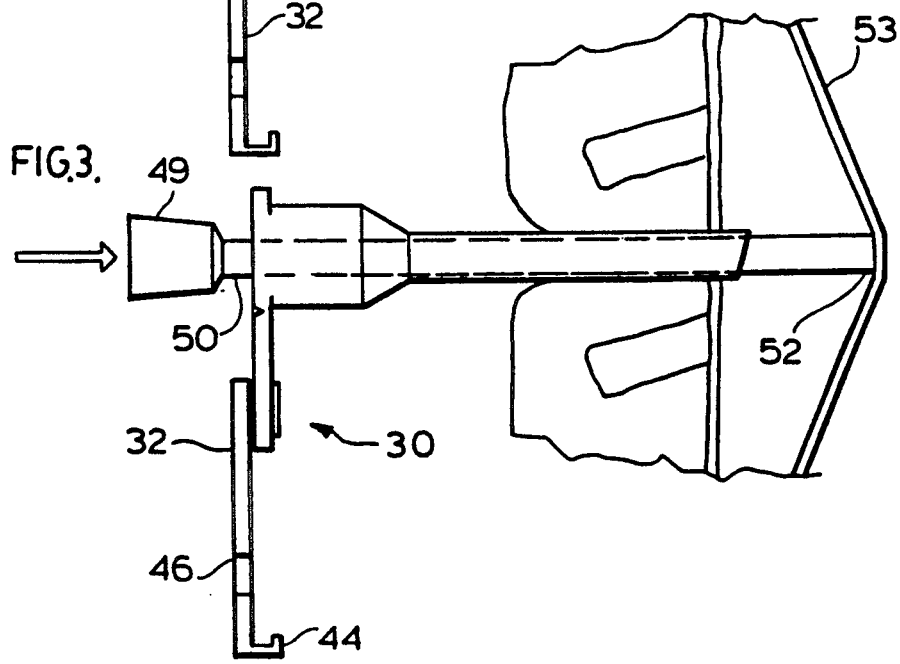

METHOD AND SYSTEM FOR INSERTING SPINAL CATHETERS

BACKGROUND OF THE INVENTION

1. Field of the Invention

This invention relates to the field of catheters and, more particularly, relates to a method and to a system for inserting catheters for administering spinal anaesthesia.

2. Description of the Prior Art

Catheter placement devices and related methods involve puncturing of a membrane or like tissue by means of a hollow needle within which a catheter is introduced to the desired location, and the needle and related accessories removed leaving the catheter in place. The hole formed in the tissue by the needle usually is larger than the diameter of the catheter allowing fluids to leak from one side of the membrane to the other to cause severe discomfort to the patient. U.S. Pat. No. 4,417,886 issued Nov. 29, 1983 discloses a catheter introduction set for introducing a catheter into a small diameter blood vessel consisting of a catheter mounted on a hollow needle having a spring wire guide therein. In use, the hollow needle is first inserted into the blood vessel, the spring wire guide is advanced into the blood vessel as far as possible and the catheter then advanced on the spring wire guide into the blood vessel. The spring wire guide and needle are removed leaving the catheter in the blood vessel.

U.S. Pat. No. 4,655,750 issued Apr. 7, 1987 discloses another embodiment of catheter system for placement of a flexible catheter into the lumen of an artery or vein which includes a guide wire adapted to be advanced into the lumen and a catheter advanced along the guide wire until placement is achieved.

U.S. Pat. No. 4,529,399 issued Jul. 16, 1985 discloses a method and apparatus for placing a catheter in which a hole is made in a vessel wall by a needle outside a catheter and the catheter advanced on a stylet.

Epidural and spinal anaesthesia require the administration of an anaesthetic agent into the epidural or subarachnoid spaces respectively of the spine. Epidural anaesthesia requires substantially more anaesthetic agent than spinal anaesthesia and, if the anaesthetist inadvertently penetrates the dura-arachnoid membrane while endeavouring to administer an anaesthetic agent to the epidural space, a dangerous quantity of anaesthetic agent can be placed in the subarachnoid space, possibly causing paralysis or even death.

U.S. Pat. No. 4,518,383 issued May 21, 1985 teaches an instrument for epidural and spinal anaesthesia in which an outer hollow Tuchy TM needle has a bent pointed tip to locate the epidural space and an inner hollow needle with a pointed tip projecting forwardly of the outer Tuchy TM needle in alignment therewith to penetrate the dura with a minimum of cutting of tissue.

U.S. Pat. No. 4,737,146 issued Apr. 12, 1988 discloses another version of epidural catheter in which a rigid epidural needle is inserted into an epidural space and an epidural catheter is introduced through the needle into the epidural space through a lateral opening in the tip of the needle.

It is an object of the present invention to provide a method and system for inserting a spinal catheter to ensure correct placement of the catheter in the subarachnoid space and to obviate leakage of cerebro-spinal fluid from the subarachnoid space into the epidural space of the spine during and after administration of continuous spinal anaesthesia.

BRIEF SUMMARY OF THE INVENTION

In accordance with one aspect of the catheter system of the invention, for the insertion of a flexible catheter through the epidural space and dura-arachnoid membrane into the subarachnoid space of a spine, the system comprises a hollow needle having a sharpened entry end for insertion into the epidural space and an exit end having a hub, a cannula with a blunt distal end adapted for placement into and axial movement within the hollow needle whereby said cannula can be advanced forwardly within the hollow needle for abutment of the blunt distal end against the dura-arachnoid membrane to place tension on the dura-arachnoid membrane, securing means adapted to be attached to the hub at the exit end of the hollow needle for locking the cannula within the hollow needle from axial movement, and a flexible catheter having a wire therein for insertion through the cannula and penetrating the dura-arachnoid membrane forming a hole, whereby the distal end of the catheter can be inserted a predetermined distance into the subarachnoid space through said hole, the cannula and the hollow needle retracted along the catheter, the securing means removed, and the wire withdrawn from the catheter.

In accordance with an aspect of the method of the invention for passing a catheter through the epidural space and dura-arachnoid membrane into the subarachnoid space of a patient's spine, the method comprises the steps of inserting a hollow needle having a sharpened entry end into the epidural space, said hollow needle having an exit end with a hub, inserting a cannula with a blunt distal end into the hollow needle and advancing the cannula forward for abutment of the blunt distal end of the cannula against the dura-arachnoid membrane to place the dura-arachnoid membrane in tension, locking the cannula from coaxial movement in the needle, inserting a flexible catheter having a wire therein through the cannula and penetrating the tensioned dura-arachnoid membrane through a hole therein whereby the distal end of the catheter can be fed a predetermined distance into the subarachnoid space through the hole formed in the dura-arachnoid membrane, and retracting the hollow needle and cannula along the catheter and withdrawing the wire while the distal end of the catheter remains inserted in the said subarachnoid space.

In accordance with another aspect of the present invention, the dura-arachnoid can be pierced with a sharp stylet to form a hole prior to insertion of the catheter with a wire.

I have found that the blunt end of a cannula can be provided by a splayed end of the cannula for effective abutment against the dura-arachnoid membrane to place the membrane in tension.

As an alternative to the catheter, a flexible or semi-rigid spinal needle can be inserted through the cannula to allow the single administration of a spinal anaesthetic. Accordingly, the method and system of the invention have utility in the insertion of catheters and needles for continuous and single administrations of anesthetics.

In accordance with an aspect of the system of the invention, for the insertion of a flexible catheter through the epidural space and dura-arachnoid membrane into the subarachnoid space of a spine, the system comprises a hollow needle having a sharpened entry end for insertion into the epidural space and an exit end having a hub, a cannula with a splayed distal end adapted for placement into and axial movement within the hollow needle whereby said cannula can be advanced forwardly within the hollow needle for abutment of the splayed distal end against the dura-arachnoid membrane to place tension on the dura-arachnoid membrane, securing means adapted to be attached to the hub at the exit end of the hollow needle for locking the cannula within the hollow needle from axial movement, and a flexible catheter having a wire therein for insertion through the cannula and penetrating the dura-arachnoid membrane forming a hole, whereby the distal end of the catheter can be inserted a predetermined distance into the subarachnoid space through said hole, the cannula and the hollow needle retracted along the catheter, the securing means removed, and the wire withdrawn from the catheter.

In accordance with an aspect of the method of the invention for passing a catheter through the epidural space and dura-arachnoid membrane into the subarachnoid space of a patient's spine, the method comprises the steps of inserting a hollow needle having a sharpened entry end into the epidural space, said hollow needle having an exit end with a hub, inserting a cannula with a splayed distal end into the hollow needle and advancing the cannula forward for abutment of the splayed distal end of the cannula against the dura-arachnoid membrane to place the dura-arachnoid membrane in tension, locking the cannula from coaxial movement in the needle, inserting a flexible catheter having a wire therein through the cannula and penetrating the tensioned dura-arachnoid membrane through a hole herein whereby the distal end of the catheter can be fed a predetermined distance into the subarachnoid space through the hole formed in the dura-arachnoid membrane, and retracting the hollow needle and cannula along the catheter and withdrawing the wire while the distal end of the catheter remains inserted in the said subarachnoid space.

In accordance with another aspect of the present invention, as an alternative to inserting a flexible catheter containing a wire, a fine flexible or semi-rigid spinal needle can be passed through the cannula and penetrate the tensioned dura-arachnoid membrane for insertion into the subarachnoid space for the administration of single dose spinal anaesthesia.

BRIEF DESCRIPTION OF THE DRAWINGS

The method and apparatus of the invention will now be described with reference to the accompanying drawings, in which:

FIG. 1 is an elevation of an epidural needle, with syringe, inserted into the epidural space of a spine;

FIG. 2 is an elevation showing a cannula inserted into the epidural needle;

FIG. 3 is an elevation showing the cannula extended to tension the dura-arachnoid membrane;

DESCRIPTION OF THE PREFERRED EMBODIMENTS

Figure 4:
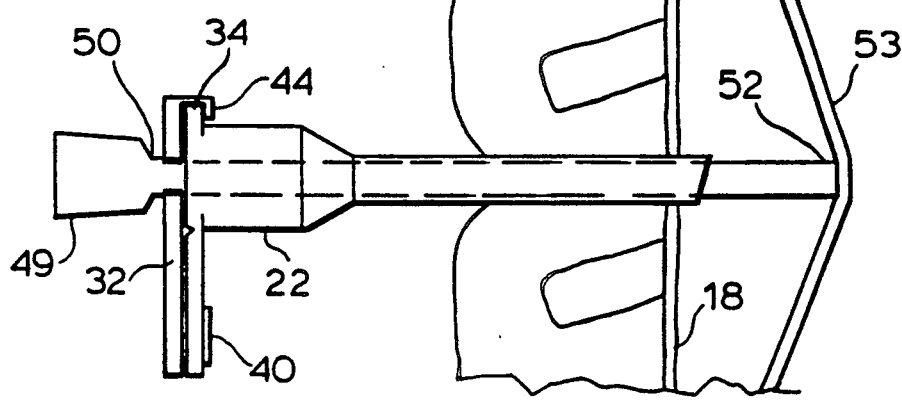
FIG. 4 is an elevation showing the cannula advanced and locked in place by a clamp.

FIG. 1 of the drawings illustrates the placement of a hollow epidural needle 10 having a sharpened end 12 inserted into the back 14 of a patient between the spinous processes 16 of the vertebrae and through the ligamentum flavum 18 into the epidural space 20. The opposite end of needle 10 has a hub 22 having a conventional conical interior for receiving the forward extension 24 of a syringe 26 and a pivot clamp or the like connector 30 shown in more detail in FIGS. 10, 11 and 12.

Figure 10:
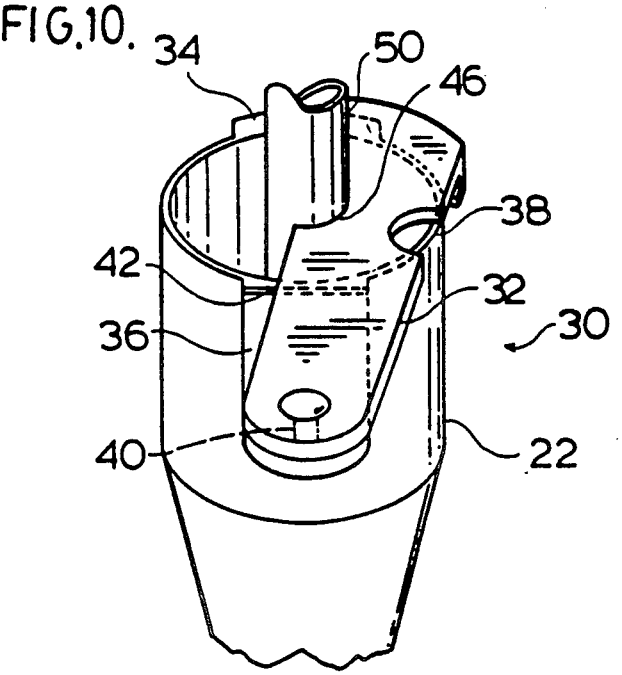
FIG. 10 is a perspective view in more detail of the hub of the epidural needle showing the clamp engaging the cannula.
Figure 11:
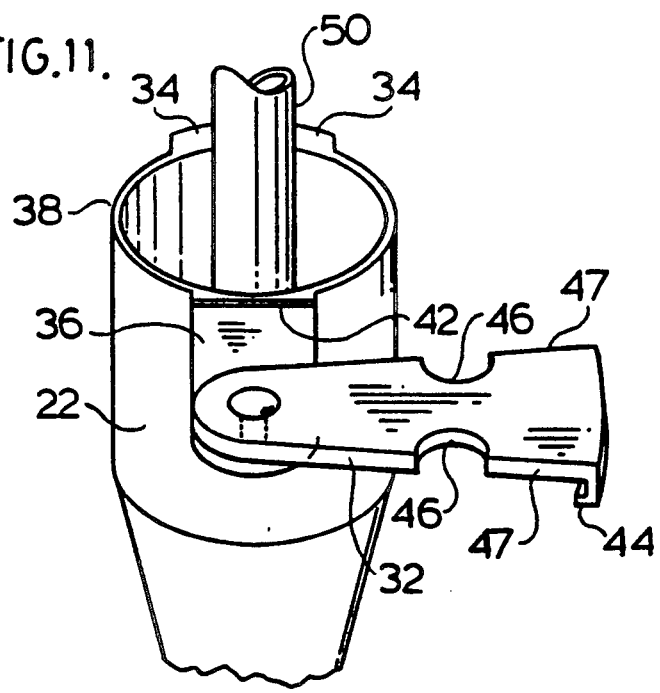
FIG. 11 is a perspective view of the circular clamp illustrated in FIG. 10 released from the cannula.
Figure 12:
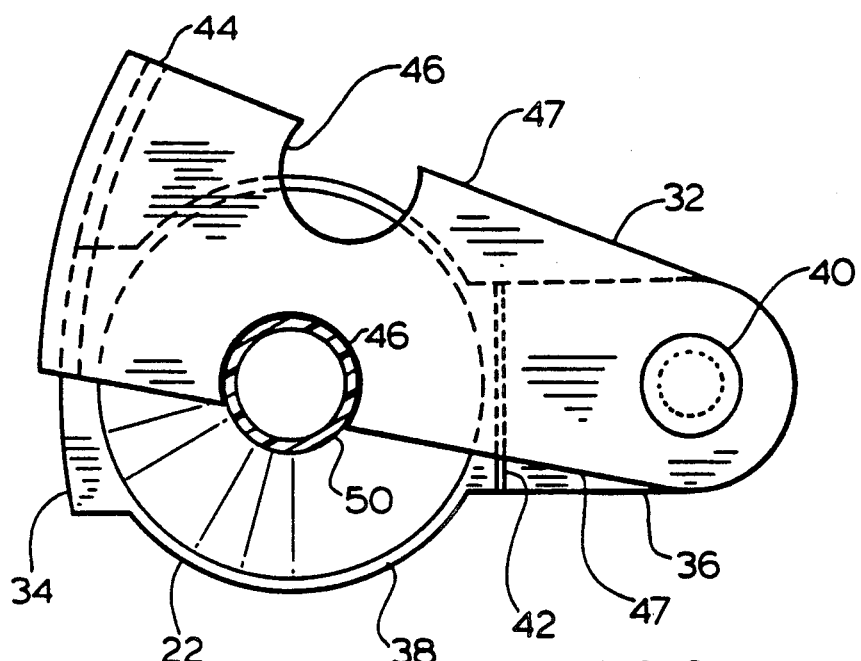
FIG. 12 is a plan view of the clamp in its locking position corresponding to FIG. 10.

With reference now to FIGS. 10, 11 and 12, pivot clamp 30 comprises a clamp arm 32 pivotally mounted on lateral extension to tab 36 formed adjacent the edge 38 of hub 22 by a stud 40. A transverse line of weakness 42 is formed in tab 36 to permit separation of tab 36 from hub 22 for reasons which will become apparent as the description proceeds.

Clamp arm 32 has a peripheral reverse flange 44 adapted to overlap and engage flange 34 of hub 22 when clamp 32 is pivotted to the operative position shown in FIGS. 4, 10 and 12. An opening 46 on each of side edge 47 of clamp arm 32 defines slightly more than a semi-circle with a diameter substantially equal to the diameter of a cannula, to be described, whereby the clamp arm 32 can be snap-fitted over the cannula for frictional engagement, as shown most clearly in FIGS. 10 and 12.

With reference now to FIG. 2, cannula 50 having a blunt distal end 52 and a blunt proximal end 49 has a diameter slightly less than the interior diameter of the needle 10 to allow placement into and coaxial movement within needle 10 such that the distal end 52 of cannula 50 can be advanced forwardly for alignment with the end 12 of needle 10 when mark 51 on the cannula is aligned with the end of needle hub 22. The entrance to the lumen of the cannula at the proximal end 49 is of a widened or funnel shape in order to permit the easy insertion of the catheter with a sharp internal wire protruding from it, thereby avoiding the bending of the tip of the wire at the end of the cannula.

With reference now to FIGS. 3 and 4, cannula 50 with blunt end 52 is advanced forwardly to place dura-arachnoid membrane 53 in tension and the cannula locked from axial movement by pivotting clamp arm 32 upwardly as viewed in FIGS. 4-9 of the drawings such that cannula 50 is frictionally engaged by the wall of an opening 46 when clamp arm 32 is snap-fitted thereover with reverse flange 44 engaging flange 34 of needle hub 22.

Figure 5:
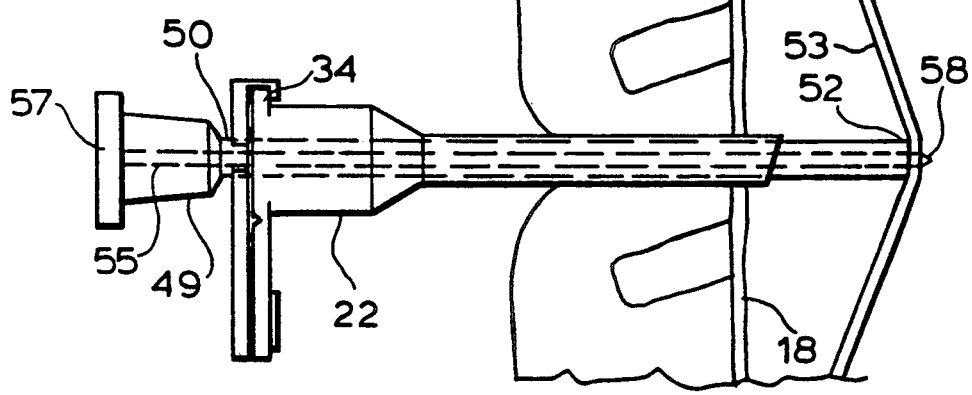
FIG. 5 is an elevation showing a sharply pointed stylet inserted into the cannula for piercing the dura-arachnoid membrane.
Figure 6:
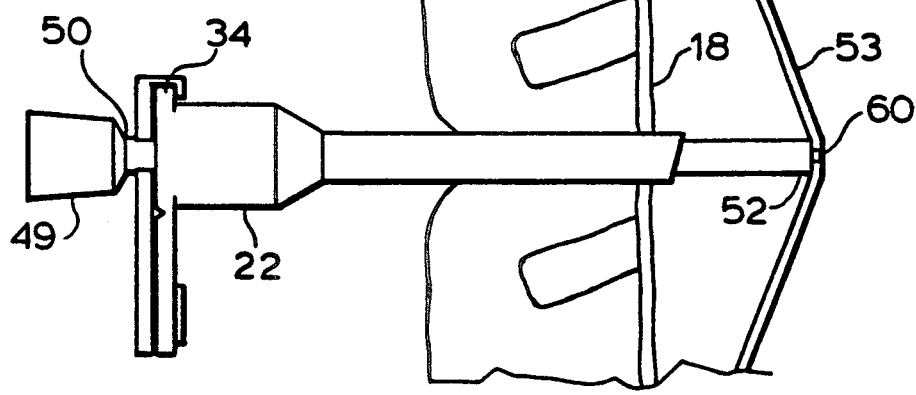
FIG. 6 is an elevation showing a hole pierced in the dura-arachnoid membrane.

FIG. 5 illustrates a sharp stylet 55 advanced through cannula 50 to pierce the taut dura-arachnoid membrane 53 by pointed tip 58 to form a hole 60 (FIG. 6) when flanged head 57 abuts the proximal end 49 of cannula 50. Stylet 55 preferably would have a diameter about the same as or slightly less than the external diameter of catheter 54 to ensure a tight fit of the catheter in hole 60 to prevent the flow of cerebral-spinal fluid from the sub-arachnoid space into the epidural space.

Figure 7:
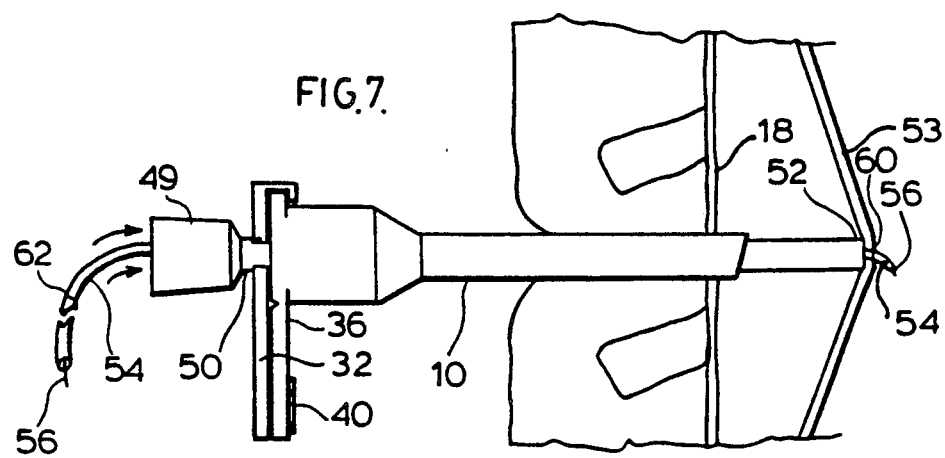
FIG. 7 is an elevation showing a catheter with a wire slidably inserted therein penetrating a hole in the dura-arachnoid membrane, the end of the wire protruding slightly beyond the end of the catheter.
Figure 8:
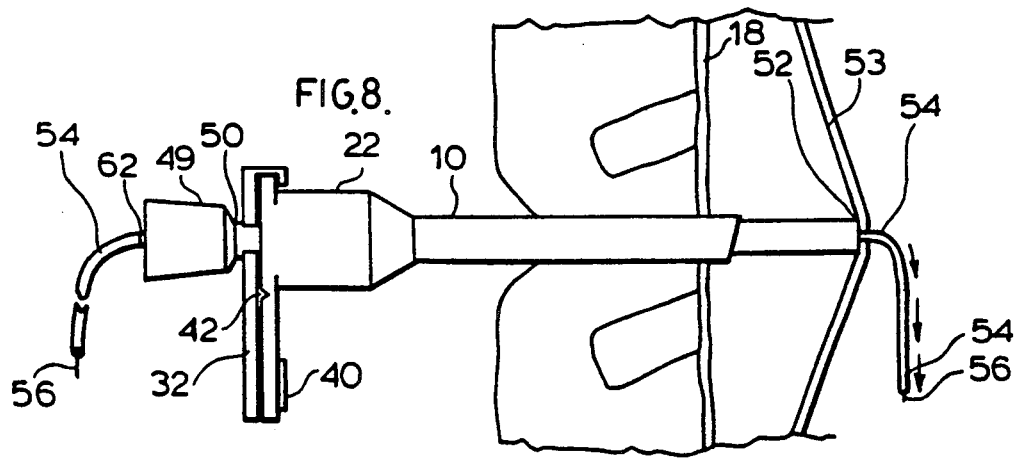
FIG. 8 depicts the advance of the catheter with the wire a desired distance into the subarchnoid space, as indicated by a mark on the catheter.

A catheter 54 with an interior wire 56 slidably mounted therein having an end projecting beyond the forward end of catheter 54 is inserted into cannula 50 and advanced forwardly to enter hole 60, as shown in FIG. 7. Catheter 54 can be advanced through hole 60 in dura-arachnoid membrane 53 a desired length as indicated by mark 62 on the catheter by pushing catheter 54 with stiffening wire 56 forwardly through the dura-arachnoid membrane 53 until mark 62 on cather 54 is aligned with the proximal end of cannula hub 49, as shown in FIG. 8.

It may be preferred not to use stylet 55, in which case wire 56 would be sharply pointed and would extend beyond the tip of catheter 54 to pierce the dura-arachnoid membrane 53 when catheter 54 is advanced against membrane 53.

Figure 9:
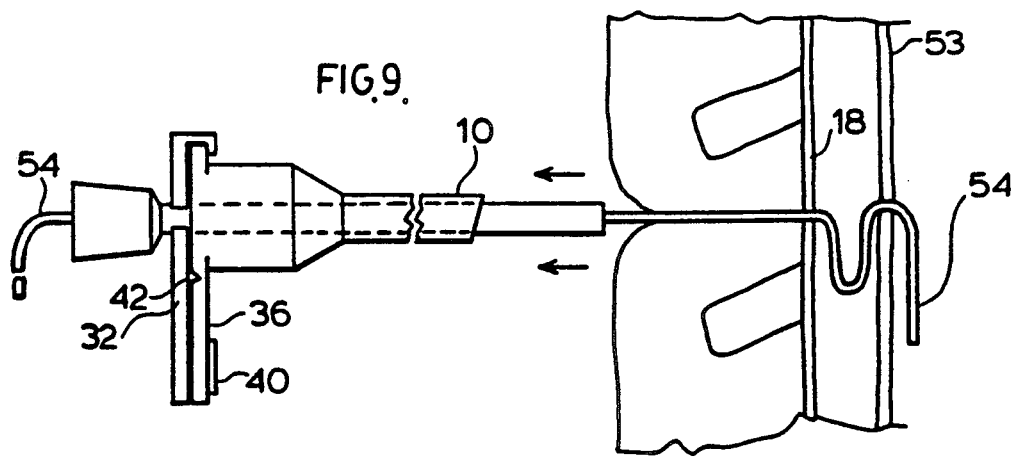
FIG. 9 is an elevation showing the withdrawal of the cannula with epidural needle, and wire, from the patient with the catheter left in site.
Figure 13:
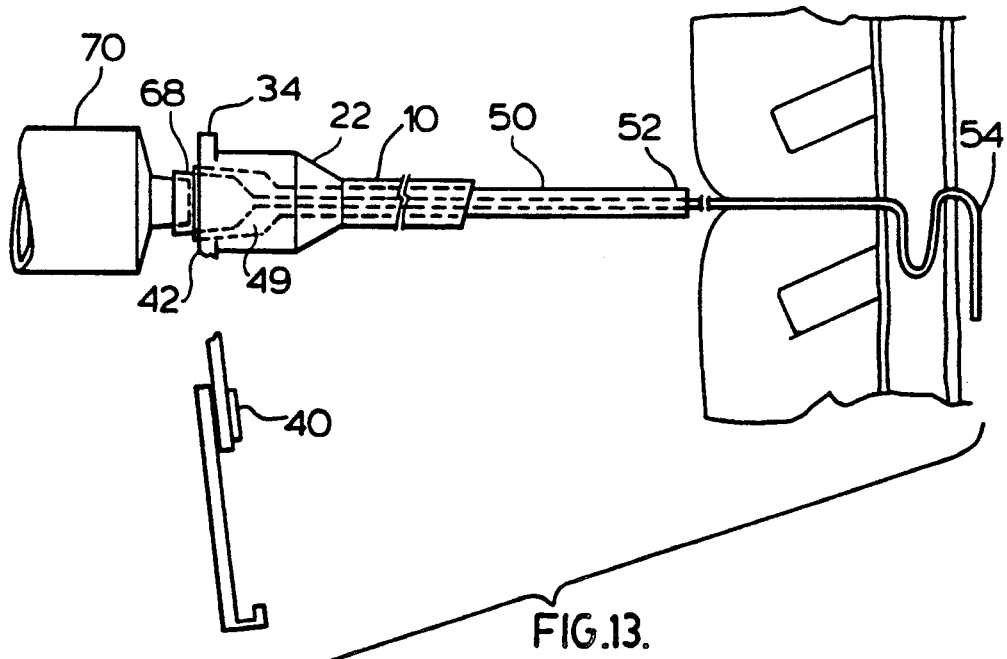
FIG. 13 is an elevation of the cannula and epidural needle frictionally connected together at the hub end of the catheter, the clamp separated from the hub of the epidural needle, and with a syringe inserted into the catheter hub.

When the catheter 54 has been extended to its desired length into the subarachnoid space through the dura-arachnoid membrane 53, as indicated by lining up mark 62 on catheter 54 with the proximal end 49 of cannula 50, epidural needle 10 with cannula 50 attached thereto by clamp 32 is removed from the patient, with the catheter 54 remaining in position, as typified in FIG. 9. With reference to FIG. 13, cannula 50 is shown in needle 10 so that proximal end 49 is firmly inserted into hub 68 at the free end of catheter 54. Clamp 32 is removed from cannula 50 and broken off at line 42. Hub 22 of needle 10 is then wedged onto hub 68 of catheter 54. A sufficient length of catheter 54 is provided to permit taping of the catheter to the patient with the epidural needle and cannula connected together in such a manner that the cannula prevents the catheter from being cut by the sharp end of the needle.

An anaesthetic can be continuously administered to the patient through the catheter 54 by syringe 70 which is coupled either directly or by means of an extension tubing to hub 68 of catheter 54 which is fitted tightly into the end 49 of cannula 50.

Figure 14:
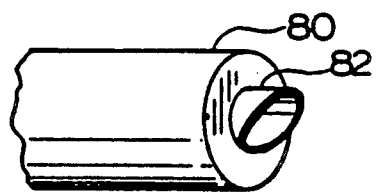
FIG. 14 is an enlarged view of the end of another embodiment of cannula.

FIG. 14 illustrates an embodiment of cannula in which the blunt distal end 80 has an inner bevelled, i.e. sharp, extension to pierce the dura-arachnoid membrane while maintaining the membrane taut.

Figure 15:
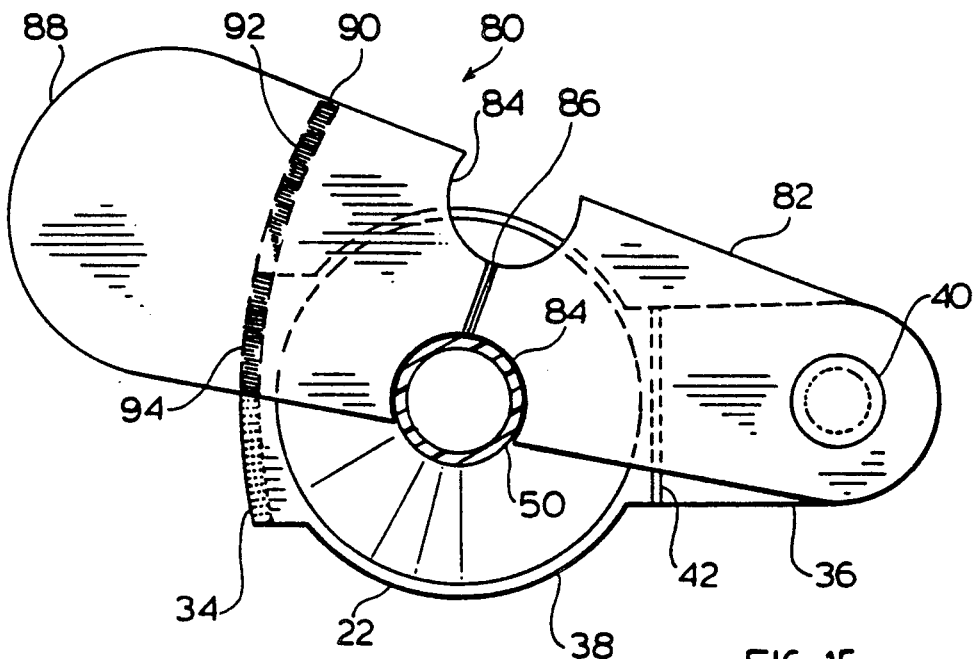
FIG. 15 is a plan view of another embodiment of pivot clamp.
Figure 16:
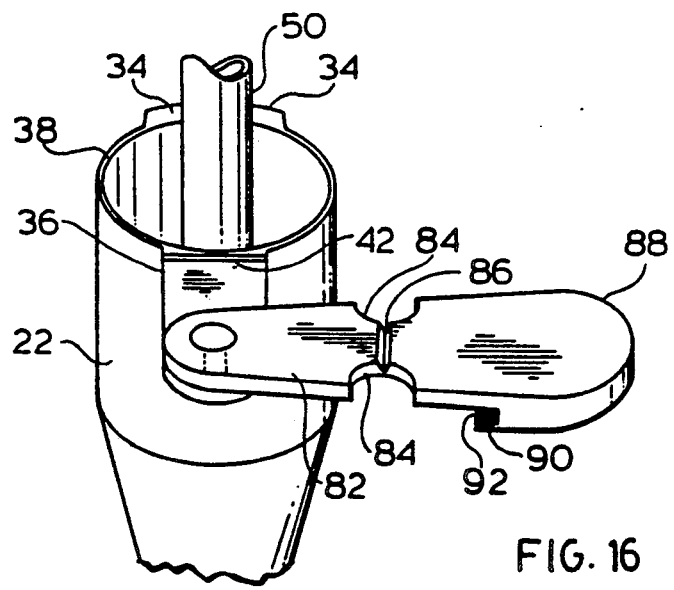
FIG. 16 is a perspective view of the pivot clamp shown in FIG. 15.

FIG. 15 and 16 illustrate another embodiment of pivot clamp 80 in which clamp arm 82, having over-centre semi-circular side openings 84 adapted to snap-fit onto cannula 50, has a transverse line of weakness formed by surface notch 86 interconnecting openings 84. The free end 88 of clamp arm 82 is extended to provide leverage to facilitate the breaking of clamp arm 82 to free cannula 50, when desired.

Reverse flange 90 formed in the underside of clamp arm 82 preferably has serrations 92 adapted to engage mating serrations 94 formed in the underside of rim flange 34 to effectively lock clamp 80 against cannula 50 by a friction fit of cannula 50 in an opening 84.

Figure 17:
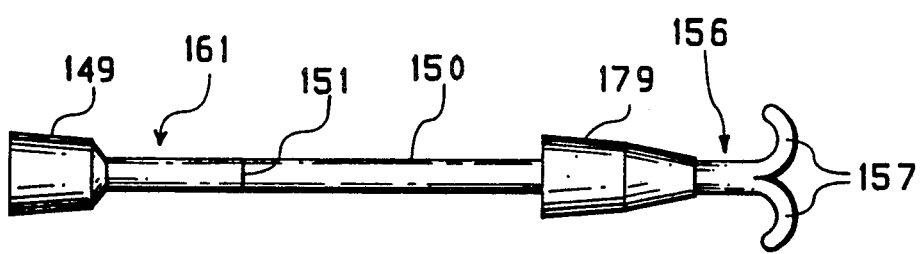
FIG. 17 is an elevation of a cannula with a slidable sleeve on the shaft of the cannula.

With reference to the drawings, FIG. 17 illustrates cannula 161 with shaft 150, splayed distal end 156, and blunt proximal end 149. The distal end 156 splays into one or more flexible tabs 157 which curl backwards (i.e. proximally) when in neutral or resting position. Sleeve 179 fits slidably over shaft 150 and has a conical exterior to fit into hub 122 of epidural needle 110, as seen in FIGS. 19-29. The distal end 156 of cannula 161 preferably is formed of resilient plastic material and is splayed radially outwardly such that the tabs are resiliently biased in an outward direction.

Figure 17A:
FIG. 17(a) is a plan view of the cannula showing the end splayed into one tab.
Figure 17B:
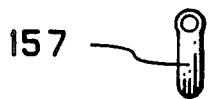
FIG. 17(b) is a plan view of the cannula showing the end splayed into four tabs.

FIG. 17(a) is a plan view of hollow cannula shaft 150 with the distal end 156 splayed outwardly to form single tab 157. FIG. 17(b) is a plan view of cannula shaft 150 showing another embodiment wherein the distal end of the cannula shaft 150 is splayed into four tabs 157. It will be understood that the distal end 156 of cannula 161 can be composed of one or more tabs 157 which splay radially outwardly in a curled fashion.

Figure 18:
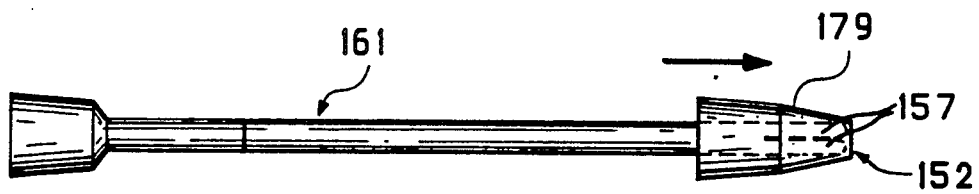
FIG. 18 is an elevation of the cannula with the sleeve slid forward to hold the previously splayed tab(s) within the sleeve in a straightened position, ready to enter the epidural needle.

Sleeve 179 slides axially over tabs 157 to hold them in a non-splayed or straightened position pointing distally, as shown in FIG. 18. When in this position, tabs 157 collectively form end 152 of cannula 161. Sleeve 179 is slid to this position just prior to use.

Figure 19:
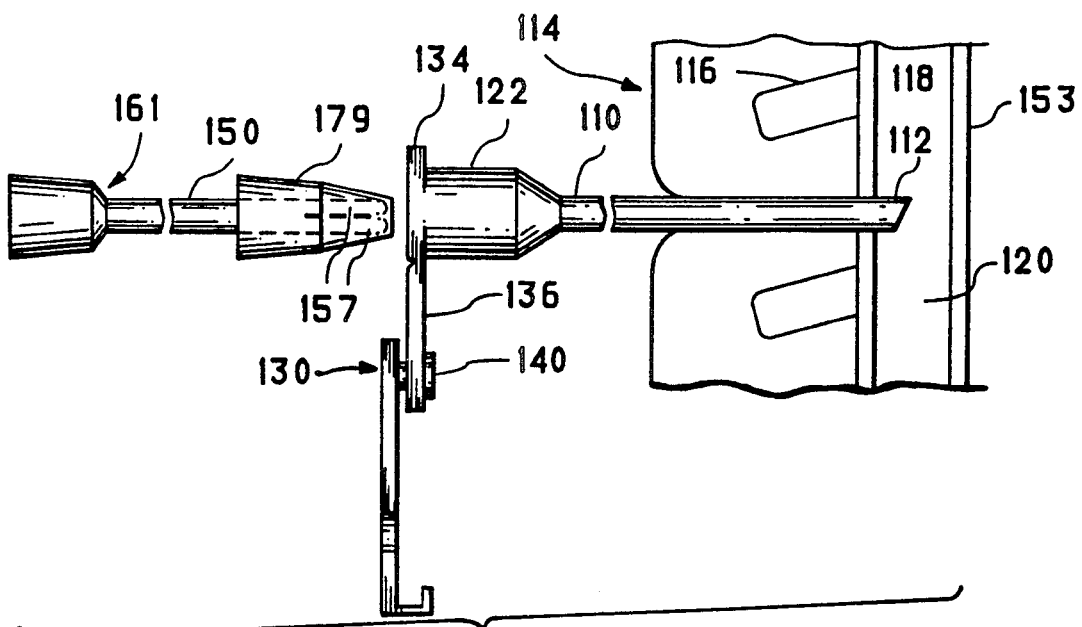
FIG. 19 is an elevation of the cannula poised about to enter the epidural needle with is inserted into the epidural space of the spine.

FIG. 19 illustrates the placement of hollow epidural needle 110 having a pointed end 112 inserted into the back 114 of a patient between the spinous processes 116 of the vertebrae, and through the ligamentum flavum 118 into the epidural space 120. The opposite end of the needle 110 has a hub 122 having a conventional conical interior for receiving a standard forward extension of a syringe and for receiving sleeve 179. A pivot clamp or the like connector 130 is formed integral therewith. Cannula 161 with sleeve 179 holding tabs 157 straight is shown in a position to enter hub 122 of epidural needle 110. Shaft 150 of cannula 161 has a diameter slightly less than the interior diameter of epidural needle 110 to allow placement into and forward coaxial movement within needle 110. During this forward movement, tabs 157 are held straight by needle 110 until they emerge from needle end 112 into the epidural space 120.

Figure 20:
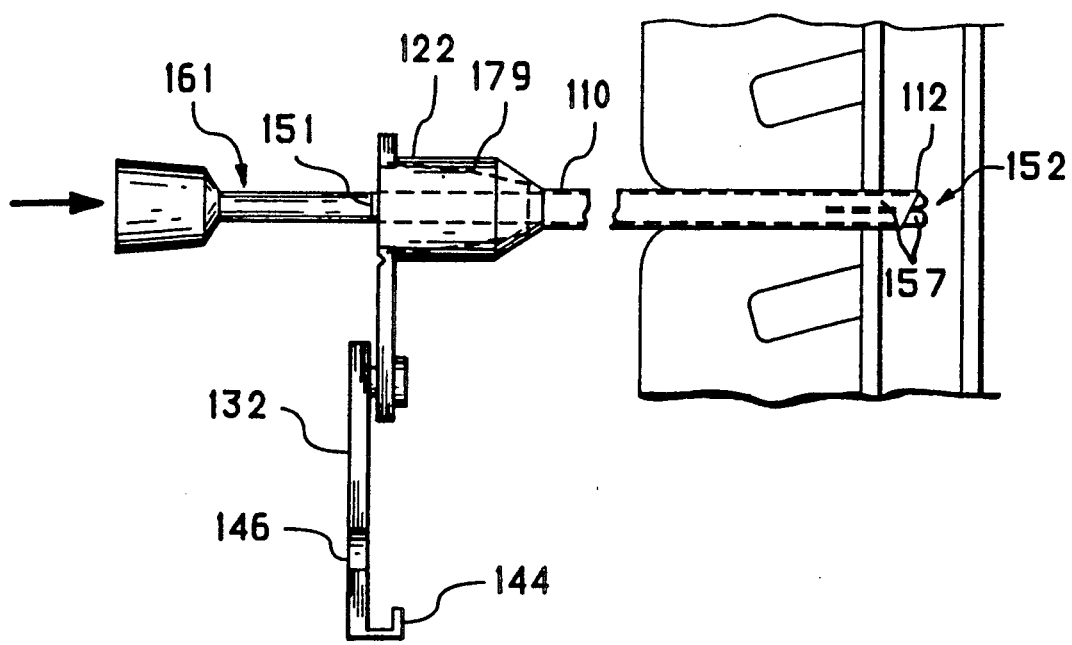
FIG. 20 is an elevation showing the cannula advanced coaxially through the epidural needle with the sleeve of the cannula located in the hub of the epidural needle and the tip of the cannula co-extensive with the tip of the epidural needle.
Figure 21:
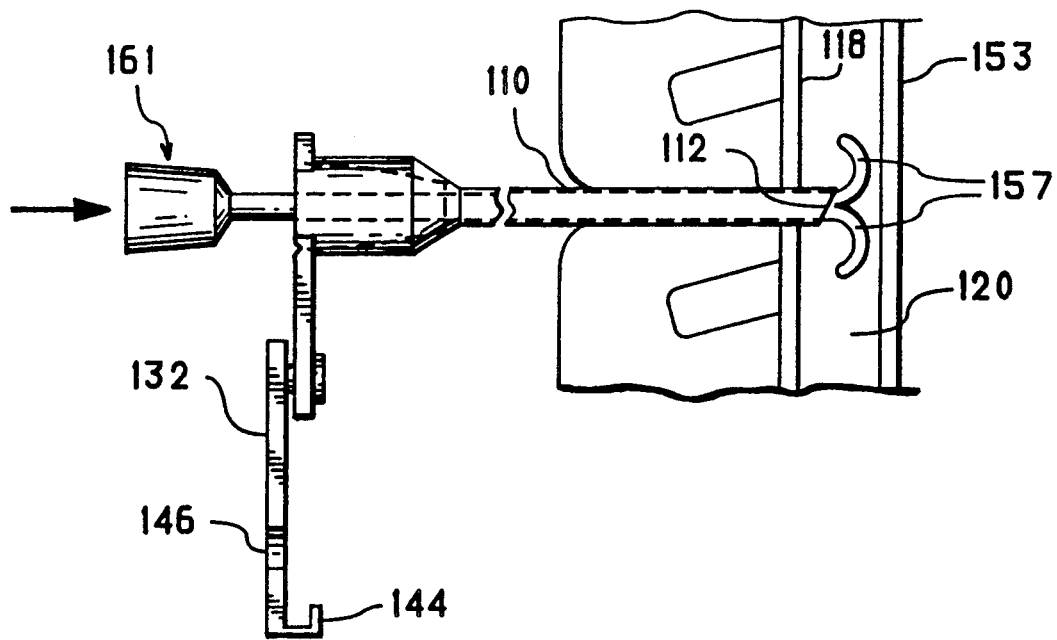
FIG. 21 is an elevation showing the cannula advanced to permit the tabs of the cannula to become splayed outwardly within the epidural space.

FIG. 20 shown cannula 161 advanced coaxially within epidural needle 110 so that the distal end 152 of cannula 161 is coextensive with the distal end 112 of epidural needle 110 when line 151 on the cannula is even with hub 122 of the epidural needle 110. Tabs 157 of the cannula are still held straight pointing distally inside epidural needle 110. With reference to FIG. 21, cannula 161 is advanced axially distally and tabs 157 emerge from end 112 of epidural needle 110 to splay outwardly to resume their original open curled shape in epidural space 120.

Figure 22:
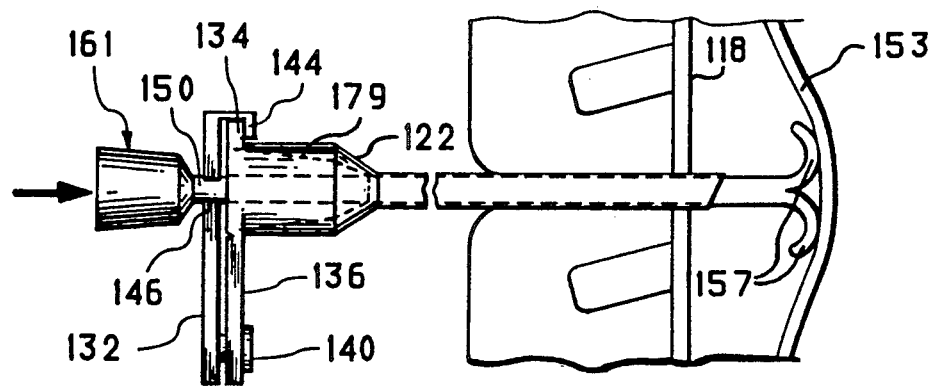
FIG. 22 is an elevation showing the cannula advanced to tension the dura-arachnoid membrane and the cannula locked in this position by a clamp incorporated into the hub of the epidural needle.

With reference now to FIG. 22, cannula 161 is advanced further so the pen tabs 157 push the dura-arachnoid membrane 153 forward and place it in tension. When the dura-arachnoid membrane is judged to be in suitable tension, the cannula is locked from coaxial movement by pivoting clamp 132 which is pivoted upwardly, as viewed in FIGS. 22 through 26, such that the cannula shaft 150 is frictionally engaged by the wall of an opening 146 when clamp arm 132 is snap-fitted thereover with reverse flange 144 engaging flange 134 of hub 122.

Figure 23:
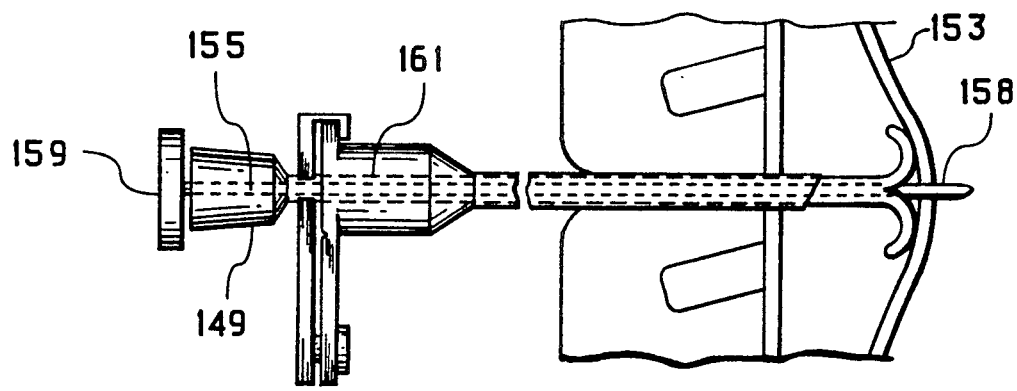
FIG. 23 is an elevation showing a pointed stylet inserted through the cannula to pierce the dura-arachnoid membrane.
Figure 24:
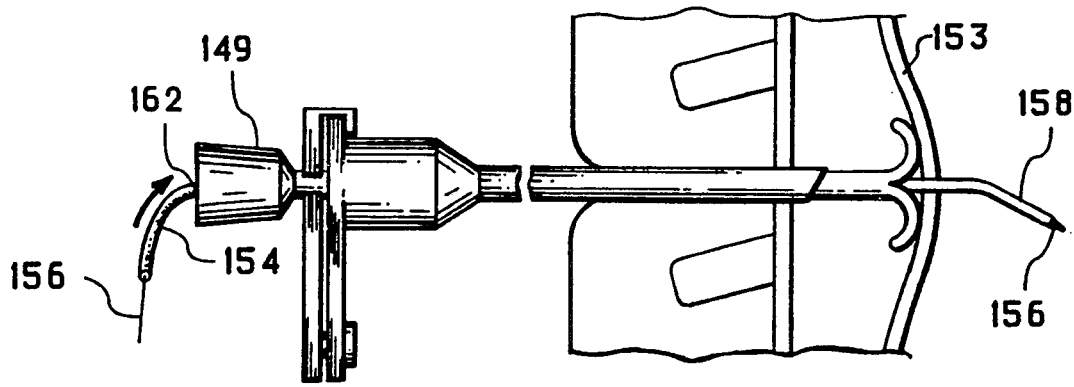
FIG. 24 is an elevation showing a catheter containing a sharpened wire protruding therefrom, inserted through the cannula, piercing the dura-arachnoid membrane, and threaded into the subarachnoid space a predetermined distance.

FIG. 23 illustrates a sharp stylet 155 advanced through cannula 161 to pierce and form a hole in the taut dura-arachnoid membrane 153 by pointed tip 158 when flanged head 159 abuts proximal end 149 of cannula 161. FIG. 24 shows stylet 155 removed and catheter 154 advanced through said hole a desired length by pushing catheter 154 containing stiffening wire 156 forwardly through the dura-arachnoid membrane 153 until mark 162 is aligned with the proximal end of hub 149. It may be preferred not to use stylet 155, in which case wire 156 would be sharply pointed and would extend beyond the tip of catheter 154 to pierce the dura-arachnoid membrane 154 when catheter 154 is advanced against membrane 153.

Figure 25:
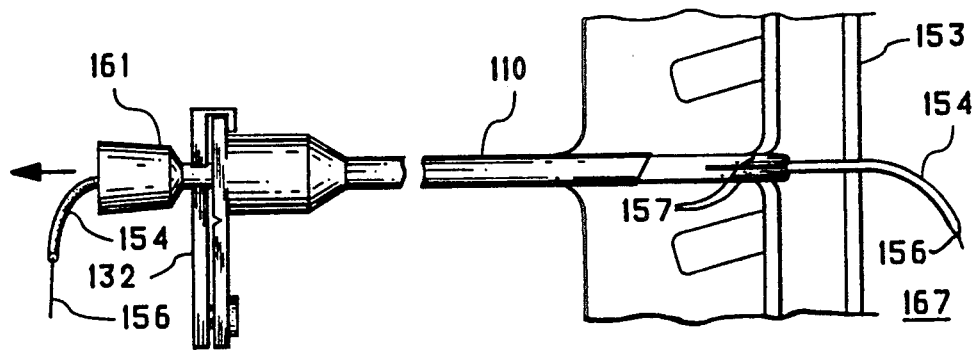
FIG. 25 is an elevation showing the catheter after the cannula-epidural needle assembly has been partially withdrawn.
Figure 26:
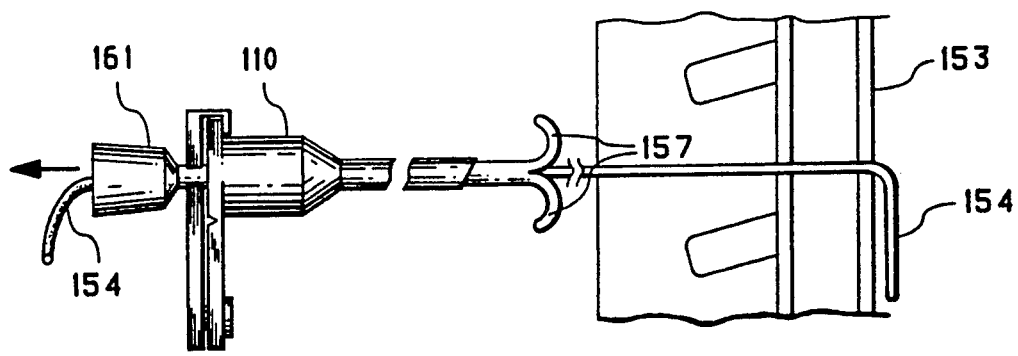
FIG. 26 is an elevation showing the cannula-epidural assembly and sharpened wire completely withdrawn leaving the catheter in place.

With reference now to FIG. 25, the epidural needle 110 with cannula 161 attached thereto by clamp 132 is partially withdrawn. This results in tabs 157 of cannula 161 becoming straightened in an extended position in the tract left by needle 110 and the dura-subarachnoid membrane 153 returning to its original non-tensioned position leaving catheter 154 with wire 156 inserted the desired distance into the subarachnoid space 167. FIG. 26 illustrates the cannula-epidural needle assembly 161-110 and wire 156 completely removed from the patient and tabs 157 of cannula 161 returned to their original splayed open position having emerged from the needle tract.

Figure 27:
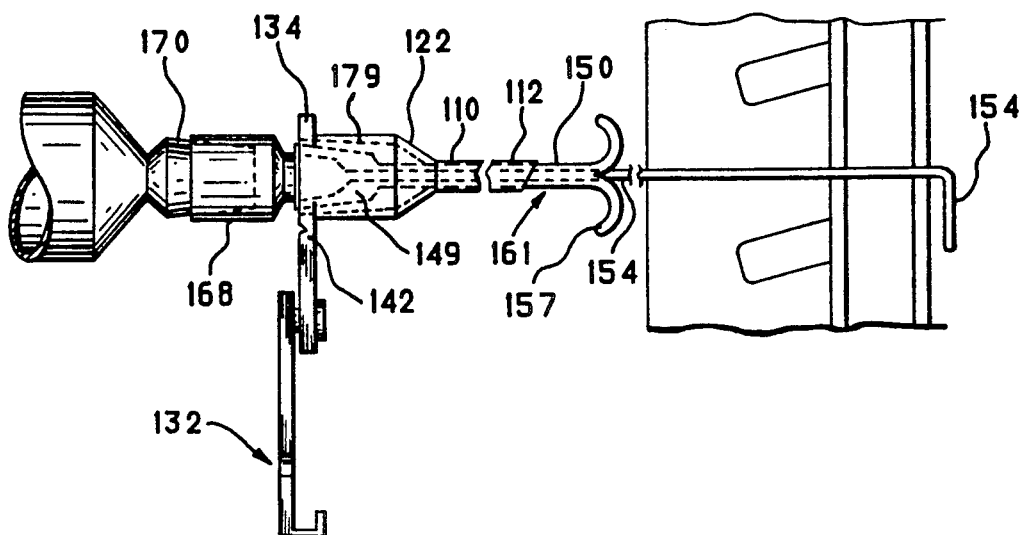
FIG. 27 is an elevation showing the catheter, cannula, sleeve and epidural needle withdrawn and frictionally attached together, a syringe frictionally attached to the catheter hub, and the clamp disassembled from the cannula.

Turning now to FIG. 27, clamp 132 is retained on cannula shaft 150 and this assembly is now slid proximally coaxially along catheter 154 to catheter hub 168. Clamp 132 is removed from cannula shaft 150 and cannula end 149 fits frictionally inside hub 168 at catheter 154. The assembled members now comprise catheter hub 168 fitted to cannula end 149 and to sleeve 179 which is fitted to needle hub 122. Shaft 150 of cannula 161 extends distally beyond the end 122 of needle 110, preventing the catheter 154 being cut by the sharp end 112 of needle 110. An anaesthetic can now be continuously or intermittently administered through catheter 154 by syringe 170 or other source of an anaesthetic solution which is coupled either directly or by means of an extension tubing to hub 168 of catheter 154.

Figure 28:
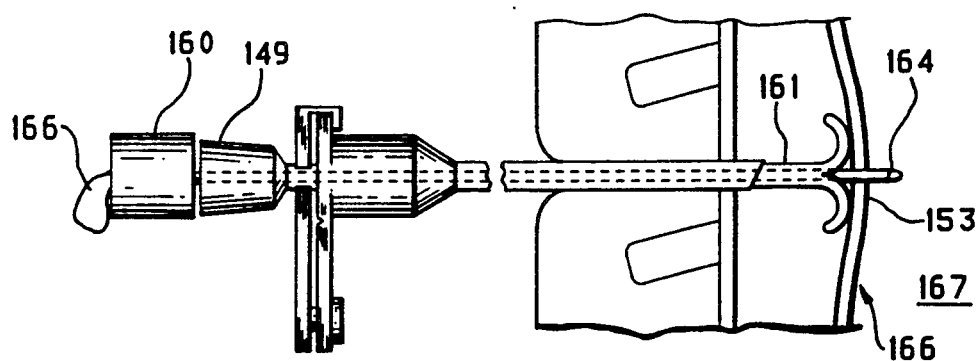
FIG. 28 is an elevation showing a spinal needle inserted through the cannula and piercing the dura-arachnoid membrane.
Figure 29:
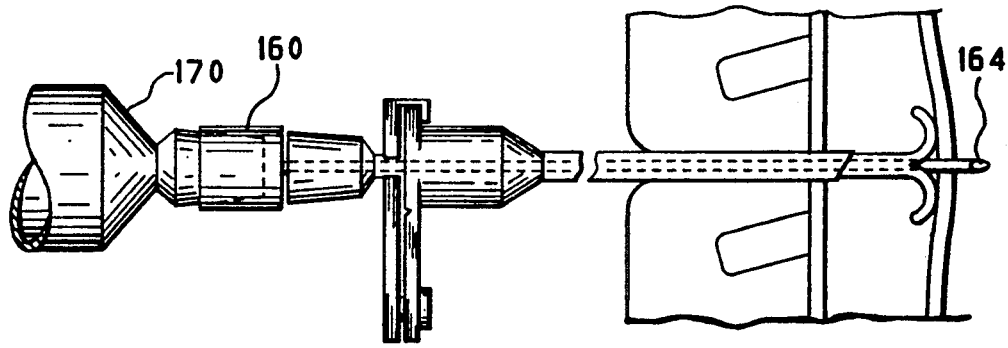
FIG. 29 is an elevation showing a syringe attached to the hub of the spinal needle.

FIG. 28 illustrates an alternate application of the method and the system of the invention for the administration of a single dose spinal anaesthetic (i.e. subarachnoid anaesthetic) through a fine flexible or semi-rigid metal spinal needle. Once the dura-subarachnoid membrane is fixed in tension as illustrated in FIG. 22, a fine spinal needle is inserted as illustrated in FIG. 28. This figure shows spinal needle 164 inserted coaxially through cannula 161 such that when hub 160 of spinal needle 164 abuts the cannula end 149, and cannot be inserted further, the spinal needle 164 has pierced the dura-arachnoid membrane 153 and the needle 164 has entered the desired distance into the subarachnoid space 167 which contains cerebral-spinal fluid 166. The cerebral-spinal fluid 166 then flows proximally through needle 164 and forms a drop 166 in the spinal needle hub 160, confirming the correct placement of needle 164 in the subarachnoid space 167. With reference to FIG. 29, a conventional syringe 170 with a standard injection tip fits into the standard interior of spinal needle hub 160 for the single administration of a spinal anaesthetic following which the entire assembly is removed.

Several alternative methods have been devised for holding the distal end of the cannula under tension against the dura-arachnoid membrane before inserting the stylet and catheter therethrough.

Figure 30:
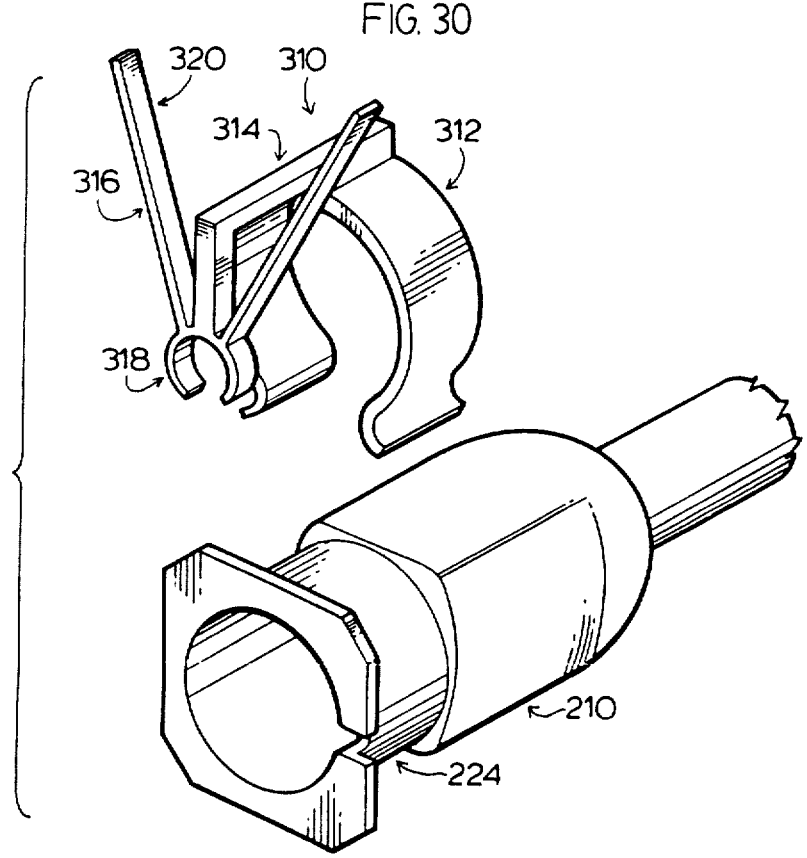
FIG. 30 is a perspective partial illustration of another embodiment of the release clip securing means.

Another means for securing the cannula within the epidural needle is shown in FIG. 30. In this embodiment, an engaging bracket 310 is so constructed as to have both an engaging means for both the cannula and for the epidural needle, which are thereby held in spaced relationship. Bracket 310 includes an engaging clip 312 of a resilient material so that if can be clipped on to needle hub 224. Support member 314 extends forward of engaging clip 312 and defines holding clip 316 at its forward end.

Clip 316 includes a pair of sprung jaws 318 on clip 316 define a central aperture coaxially aligned with the aperture defined by needle engaging clip 312. Clip 316 includes a pair of handles 320 which when compressed toward each other, direct pivotal opening action to jaws 318.

After the epidural needle is positioned, the bracket is attached to the hub 224 of epidural needle by means of clip 312. Handles 320 are then squeezed toward each other to hold jaws 318 of the clip open. The cannula is inserted to the desired distance and then handles 320 are released, allowing jaws 318 to close onto and engage the cannula so that it cannot move axially in either direction. After the catheter is inserted, the cannula and needle are removed from the patient while still clamped to each other. The cannula is usually not removed from the needle once they are assembled. After removal from the patient, the clip is removed and discarded and the proximal end of the cannula will fit tightly into the hub of the cathere, shown in FIGS. 13 and 27.

Figure 31:
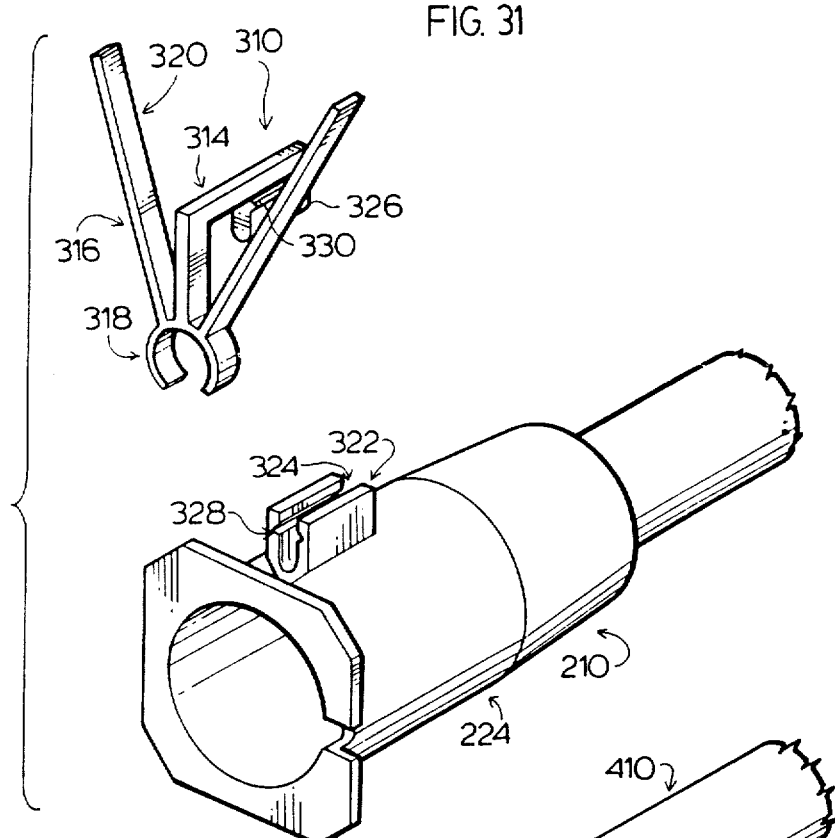
FIG. 31 is a perspective partial illustration of a modified version of the release clip of FIG. 34.

A modification of engaging bracket 310 is shown in FIG. 31. In this embodiment, needle hub 224 includes an integral tab 322 which may have a fracture line along its junction with the hub for easy break-off. Tab 322 includes a longitudinal groove 324 in its upper portion.

In place of the engaging clip shown in FIG. 30, the embodiment of FIG. 31 includes a rail clip 326 which extends along a portion of the rearward end of support member 314. Bracket 310 is thereby engaged onto needle hub 224 by aligning rail clip 326 of the bracket with central groove 324, and snapping it into position. Tab 322 is made of a resilient plastic so that the sides defining groove 324 can be separated to accommodate clip 326. A central slot 328 in groove 324 receives a corresponding rim 330 on clip 326 to hold the bracket 310 in position. The cannula coaxially positioned within the needle is then engaged by jaws 318 of the holding clip portion 316 in the manner described above.

With the cannula so secured in position against the dura-arachnoid membrane, a stylet is directed down through the cannula to pierce the membrane so that a spinal catheter can then be directed through the opening. The cannula and epidural needle are removed from the patient still clamped together. The clamp is disengaged from the epidural needle by breaking off tab 322 along its fracture line.

Figure 32A:
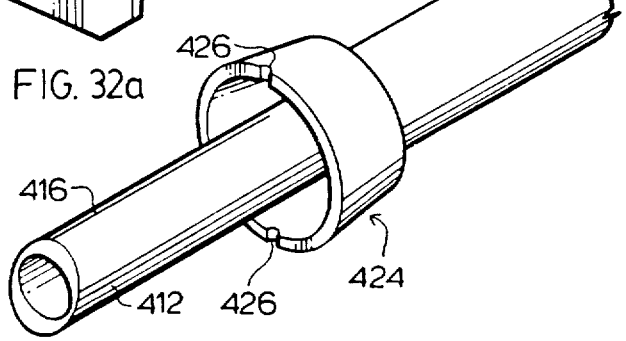
FIG. 32a is a perspective partial illustration of another embodiment of the securing means using a cannular and a needle each of elliptical cross-section.
Figure 32B:
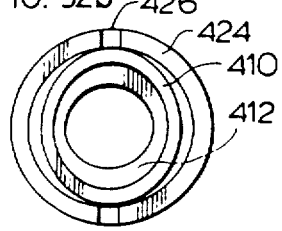
FIG. 32b is a cross-sectional illustration in schematic form showing the elliptical cannular in axial alignment within the elliptical epidural needle.

It must be appreciated that many mechanical alternatives can be used to secure the cannula coaxially within the epidural needle and hold it in fixed extension. For example, another method would involve the use of a needle having an oval cross-section. This is shown in FIG. 32a and 32b in which an epidural needle 410 having an elliptical cross-section is used in conjunction with a cannula 412 having a similar external elliptical cross-section but small enough to fit axially through the needle when their respective cross-sections are aligned. Cannula 412 includes a pair of oppositely positioned lines 416 which are respectively aligned with the major cross-sectioned axis of the elliptical cannula 412 which is rounded to fit a standard syringe.

Needle hub 424 includes a pair of oppositely positioned grooves 426 which are also so positioned as to be aligned with the major cross-sectioned axis of the elliptical needle. The cannula is drawn down through the needle in the manner described above. The major axis of cannula and needle can be easily aligned by aligning lines 416 on cannula 412 with grooves 426 on hub 424. This alignment is schematically illustrated in FIG. 32b. When the cannula is extended through the needle to a predetermined point, such as engagement with the dura-arachnoid membrane, the cannula is rotated on its longitudinal axis approximately 90 degrees so that the major cross-sectioned axis of the cannula is aligned with the minor cross-sectioned axis of the needle thereby providing a secure wedging fit therein. The cannula is thereby locked in special engagement within the needle. The cannula can be unlocked by rotating the cannula back to its original position with respect to the needle.

It was found that one method for controlling the placement of the catheter tip is to intrinsically bend the catheter to about 90 degrees about 2 cm. from its distal end and include a black indicator line into the catheter on the side which is convex of the bend. The catheter would be held straight by the cannula and the stiffening wire during insertion through the dura-arachnoid membrane. When the catheter is in the spinal canal a disting of 2 cm, the stiffening wire is removed and the catheter would resume its intrinsic bend in the desired direction since it has a satisfactory degree of resiliency. The catheter would be inserted into and through the cannula with the black line (hence the end of the catheter) directed either cephalad (towards the patient's head) or caudad (towards the patient's feet) as desired.

It is also advantageous that the wire should have an intrinsic bend of about 90 degrees as well. This bend could be located about 25 cm from its distal end. It was observed that when the tip of the wire contact the dura-arachnoid membrane, the wire is occasionally pushed back up the catheter. An intrinsic bend in the wire at a location which will be beyond the end of the catheter at that point in the operation will prevent it drawing back. However, the wire is sufficiently resilient that when it has to be withdrawn from the catheter, it can be pulled through without any significant additional effort.

It will be understood that modifications can be made in the embodiment of the invention illustrated and described herein without departing from the scope and purview of the invention as defined by the appended claims.

I claim:

1. A catheter system for the insertion of a flexible catheter through the epidural space and dura-arachnoid membrane into the subarachnoid space of the spine of a patient comprising:

(a) a hollow needle having a sharpened tip, for insertion into the epidural space, and an exit end having a hub;

(b) a cannula with a blunt distal end adapted for placement into and for coaxial movement within the hollow needle, whereby said cannula can be advanced forwardly within the hollow needle for abutment of the blunt distal end against the dura-arachnoid membrane to place the dura-arachnoid membrane in tension;

(c) securing means for engaging and restraining the cannula within the hollow needle from coaxial rearward movement therein; and (d) a flexible catheter having a wire therein for insertion through the cannula and for penetrating the dura-arachnoid membrane, whereby the distal end of the catheter can be inserted a predetermined distance through the dura-arachnoid membrane into the subarachnoid space, the cannula and the hollow needle retracted along the catheter, and the wire withdrawn from the catheter.

2. A catheter system as claimed in claim 1 in which the wire extends beyond the distal end of the catheter and said end of the wire extending beyond the distal end of the catheter is sharpened.

3. A catheter system as claimed in claim 1 in which the hollow needle and said cannula each have an elliptical cross-section of substantially the same configuration and said securing means comprises a means for axially rotating said cannula within said hollow needle whereby the major elliptical axis of said cannula is rotated out of alignment with the major elliptical axis of said hollow needle.

4. A catheter system for the insertion of a flexible catheter through the epidural space and dura-arachnoid membrane into the subarachnoid space of the spine of a patient comprising:
   a) a hollow needle having an eliptical cross-section with a sharpened tip at one end for insertion into the epidural space and an exit end at the other having a substantially cylindrical hub;
   b) a cannula having an eliptical cross-section with a blunt distal end adapted for placement into the hollow needle whereby the major cross-sectional axis of said cannula and said needle are aligned for coaxial movement of the cannula within said hollow needle, whereby said cannula can be advanced forwardly within the hollow needle for abutment of the blunt distal end against the dura-arachnoid membrane to place said membrane in tension;
   c) securing means for engaging and restraining the cannula within the hollow needle from coaxial movement therein comprising means for rotating the major cross-sectional axis of said cannula with respect to the major cross-sectional axis of said hollow needle; and
   d) a flexible catheter having a wire therein for insertion through thee cannula and for penetrating the dura-arachnoid membrane, whereby the distal end of the catheter can be inserted a predetermined distance through the dura-arachnoid membrane into the subarachnoid space, the cannula and the hollow needle retracted along the catheter, and the wire withdrawn from the catheter.

5. A catheter system as claimed in claim 4 wherein the securing means comprises an engaging bracket having a releasable engaging means at one end for securing said bracket to said needle hub and a clip member extending axially from said engaging means in rigid spaced relationship therefrom, said clip member being engagable with said cannula by means of spring activated jaws, a pair of cooperating members on said clip for pivotally actuating said jaws for engagement on said cannula whereby coaxial movement of said cannula within said hollow needle is inhibited.

6. A method for passing a catheter through the epidural space and dura-arachnoid membrane into the subarachnoid space of the spine of a patient comprising the steps of:
   (a) inserting a hollow needle having an elliptical cross-section with a sharpened tip into the epidural space, said hollow needle having an exit end with a hub;
   (b) inserting a cannula having an elliptical cross-section with a blunt distal end into the hollow needle and advancing the cannula forwardly coaxially within the needle for abutment of the distal end of the cannula against the dura-arachnoid membrane for placing the dura-arachnoid membrane in tension, and locking the cannula from coaxial movement in the needle by rotating the cannula with respect to the needle whereby the cannula makes a secure wedging fit within the needle;
   (c) inserting a flexible catheter having a stiffening wire therein through the cannula for penetrating the tensioned dura-arachnoid membrane whereby the distal end of the catheter can be fed a predetermined distance into the subarachnoid space;
   (d) retracting the hollow needle and cannula along the catheter while the catheter remains inserted in the said subarachnoid space with the stiffening wire; and
   (e) removing the stiffening wire.

7. A method as claimed in claim 6 in which the dura-arachnoid membrane is pierced with a stylet prior to insertion of the catheter with stiffening wire.

8. A system for the insertion of a flexible catheter or a fine flexible or semi rigid needle through the epidural space and dura-arachnoid membrane into the dura-arachnoid space of the spine of a patient comprising:
   (a) a hollow needle having a sharpened tip, for insertion into the epidural space, and an exit end having a hub;
   (b) a cannula with a splayed distal end having at least one flexible tab at said distal end;
   (c) a sliding sleeve for axial advancement over the splayed end of said cannula to straighten said tab(s) to allow the cannula to be placed into and introduced forwardly coaxially into the hollow needle, whereby the said sleeve remains in the hub of the needle, and the end of said cannula, after emerging from the hollow needle, splays and abuts against the dura-arachnoid membrane to place the dura-arachnoid membrane in tension;
   (d) securing means for engaging and restraining the cannula within the hollow needle from coaxial rearward movement therein;
   (e) a flexible catheter having a wire therein for insertion through the cannula and for penetrating the dura-arachnoid membrane, whereby the distal end of the catheter can be inserted a predetermined distance through the dura-arachnoid membrane into the subarachnoid space, the cannula and the hollow needle retracted along the catheter, and the wire withdrawn from the catheter; or
   (f) a flexible or semi-rigid needle having a sharpened tip for insertion through the cannula and penetration into the dura-arachnoid membrane whereby the distal end of the needle can be inserted a predetermined distance through the dura-arachnoid membrane into the subarachnoid space, and an exit end having a hub to fit a syringe.

9. A system as claimed in claim 8 in which the wire extends beyond the distal end of the catheter and said end of the wire extending beyond the distal end of the catheter is sharpened.

10. A system as claimed in claim 8 in which the securing means comprises a clamp pivotally mounted on a lateral extension of the hub of the hollow needle, said clamp having an opening formed on a side thereof for frictionally engaging and locking the cannula from coaxial movement in the hollow needle.

11. A system as claimed in claim 10 in which said lateral extension of the hub has a line of weakness formed therein adjacent the hub to permit separation of the lateral extension from the hub.

12. A catheter system as claimed in claim 8 wherein said hollow needle and said cannula each have an eliptical cross-section of substantially the same configuration and said securing means comprises a means for axially rotating said cannula within said hollow needle whereby the major eliptical axis of said cannula is rotated out of alignment with the major eliptical axis of said hollow needle.

13. A catheter system as claimed in claim 8 wherein the securing means comprises an engaging bracket having a releasable engaging means at one end for securing said bracket to said needle hub and a clip member extending axially from said engaging means in rigid spaced relationship therefrom, said clip member being engagable with said cannula by means of spring activated jaws, a pair of cooperating members on said clip for pivotally actuating said jaws for engagement on said cannula whereby coaxial movement of said cannula within said hollow needle is inhibited.

14. A method for passing a catheter through the epidural space and dura-arachnoid membrane into the subarachnoid space of the spine of a patient comprising the steps of:
(a) inserting a hollow needle having a sharpened tip into the epidural space, said hollow needle having an exit end with a hub;
(b) inserting a cannula having a splayed distal end into the hollow needle and advancing the cannula forwardly coaxially within the needle for abutment of the played distal end of the cannula against the dura-arachnoid membrane for placing the dura-arachnoid membrane in tension, and locking the cannula from coaxial movement in the needle;
(c) inserting a flexible catheter having a stiffening wire therein through the cannula for penetrating the tensioned dura-arachnoid membrane whereby the distal end of the catheter can be fed a predetermined distance into the subarachnoid space;
(d) retracting the hollow needle and cannula along the catheter while the catheter remains inserted in the said subarachnoid space with the stiffening wire; and
(e) removing the stiffening wire.

15. A method as claimed in claim 14 in which the dura-arachnoid membrane is pierced with a stylet prior to insertion of the catheter with stiffening wire.

16. A method for passing a catheter through the epidural space and dura-arachnoid membrane into the subarachnoid space of the spine of a patient comprising the steps of:
(a) inserting a hollow needle having a sharpened tip into the epidural space, said hollow needle having an exit end with a hub;
(b) inserting a cannula with a splayed forward end into the hollow needle and advancing the cannula forwardly coaxially within the needle for abutment of the splayed distal end of the cannula against the dura-arachnoid membrane in tension, and locking the cannula from coaxial movement in the needle;
(c) inserting a flexible catheter having a stiffening wire therein with an end of the wire extending beyond the distal end of the catheter coaxially through the cannula for penetrating the tensioned dura-arachnoid membrane whereby the distal end of the catheter can be fed a predetermined distance into the subarachnoid space, through a hole formed in the dura-arachnoid membrane;
(d) advancing the catheter a further predetermined distance over the wire into the subarachnoid space through the hole in the dura mater; and
(e) retracting the hollow needle and cannula along the catheter while the catheter remains inserted in the said subarachnoid space with the stiffening wire; and
(f) removing the stiffening wire.

17. A method as claimed in claim 16, in which the dura-arachnoid membrane is pierced with a stylet prior to insertion of the catheter with a stiffening wire.

18. A method for passing a flexible or semi-rigid needle through the epidural space and dura-arachnoid membrane into the subarachnoid space of the spine of a patient comprising the steps of:
(a) inserting a hollow needle having a sharpened tip into the epidural space, said hollow needle having an exit with a hub;
(b) inserting a cannula with a splayed forward end into the hollow needle and advancing the cannula forwardly coaxially within the needle for abutment of the played distal end of the cannula against the dura-arachnoid membrane for placing the dura-arachnoid membrane in tension, and locking the cannula from coaxial movement in the needle; and
(c) inserting a flexible or semi-rigid needle coaxially through the cannula for penetrating the tensioned dura-arachnoid membrane whereby the distal end of the needle rests a predetermined distance into the subarachnoid space, through a hole formed in the dura-arachnoid membrane.

* * * * *

UNITED STATES PATENT AND TRADEMARK OFFICE
CERTIFICATE OF CORRECTION

PATENT NO.  : 5,160,323
DATED       : Nov. 3, 1992
INVENTOR(S) : Daniel E. Andrew It is certified that error appears in the above-indentified patent and that said Letters Patent is hereby corrected as shown below:

On title page, insert item [60] "Related Application" as follows:
--This Application is a CIP of 07/357502, Patent No. 4,973,312--

The drawing sheets, consisting of Figs. 30-32b, should be added as shown on the attached pages.

Signed and Sealed this

Twelfth Day of April, 1994

BRUCE LEHMAN

*Attest:*

*Attesting Officer*  *Commissioner of Patents and Trademarks*